(12) United States Patent
Kim et al.

(10) Patent No.: US 10,285,979 B2
(45) Date of Patent: May 14, 2019

(54) BREAST CANCER THERAPEUTIC AGENT CONTAINING 5'-HYDROXY-5-NITRO-INDIRUBIN-3'-OXIME AS ACTIVE INGREDIENT

(71) Applicant: ANYGEN CO., LTD., Gwangju (KR)

(72) Inventors: Jae il Kim, Gwangju (KR); Seon-Myung Kim, Gwangju (KR); San Ho Kim, Gwangju (KR); Moon Young Park, Gwangju (KR)

(73) Assignee: ANYGEN CO., LTD., Gwangju (KR)

( * ) Notice: Subject to any disclaimer, the term of this patent is extended or adjusted under 35 U.S.C. 154(b) by 0 days.

(21) Appl. No.: 15/595,164

(22) Filed: May 15, 2017

(65) Prior Publication Data
US 2018/0147182 A1    May 31, 2018

(30) Foreign Application Priority Data

Nov. 25, 2016   (KR) .......................... 10-2016-157929

(51) Int. Cl.
| | |
|---|---|
| *A61K 31/404* | (2006.01) |
| *A61K 31/4155* | (2006.01) |
| *A61K 45/06* | (2006.01) |
| *C07D 209/38* | (2006.01) |
| *C07D 403/04* | (2006.01) |
| *C12Q 1/6886* | (2018.01) |

(52) U.S. Cl.
CPC ........ *A61K 31/404* (2013.01); *A61K 31/4155* (2013.01); *A61K 45/06* (2013.01); *C07D 209/38* (2013.01); *C07D 403/04* (2013.01); *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,572,923 B2 | 8/2009 | Kim et al. | |
| 8,859,783 B2* | 10/2014 | Kim ..................... | C07D 403/04 548/457 |
| 2007/0155816 A1* | 7/2007 | Kim ..................... | A61K 31/403 514/414 |
| 2010/0331327 A1* | 12/2010 | Meijer ................. | C07D 209/40 514/235.2 |
| 2012/0295948 A1* | 11/2012 | Kim ..................... | A61K 31/404 514/414 |
| 2015/0087687 A1* | 3/2015 | Brown ................. | A61K 31/404 514/414 |
| 2016/0243077 A1* | 8/2016 | Brown ................. | A61K 31/404 |

OTHER PUBLICATIONS

Verbaanderd, et al. ecancer 2017, 11:781, pp. 1-42 (Year: 2017).*
Thomas et al. Cancer Letters, vol. 325 (1), 63-71, 63(2012). (Year: 2012).*
Choi et al. J. Med. Chem. 53(9) 3693-3706 (2010). (Year: 2010).*
Subik et al. Breast Cancer (Auckl) (2010) 4, 35-41. (Year: 2010).*
Mee-Young Ahn et al., "5-Nitro-5'hydroxy-indirubin-3'-oxime (AGM130), an indirubin-3'-oxime derivative, inhibits tumor growth by inducing apoptosis against non-small cell lung cancer in vitro and in vivo", European Journal of Pharmaceutical Sciences, vol. 79, Sep. 2, 2015, pp. 122-131.
Woo-Seok Kim et al., "5'-OH-5-nitro-Indirubin oxime (AGM130), an Indirubin decivative, induces apoptosis of imatinib-resistant chronic myeloid leukemia cells", Leukemia Research, vol. 37, Jan. 19, 2013, pp. 427-433.

* cited by examiner

*Primary Examiner* — Nyeemah A Grazier
(74) *Attorney, Agent, or Firm* — MH2 Technology Law Group, LLP (57) ABSTRACT

A breast cancer therapeutic agent containing 5'-hydroxy-5-nitro-indirubin-3'-oxime as active ingredient has been disclosed. Further, a breast cancer therapeutic agent containing 5'-hydroxy-5-nitro-indirubin-3'-oxime as cyclin-dependent kinase (CDK) inhibitor, wherein said breast cancer is triple negative breast cancer (TNBC) and/or an estrogen receptor (ER) positive breast cancer including the tamoxifen-resistant estrogen receptor (ER) positive breast cancer has been disclosed.

4 Claims, 9 Drawing Sheets

BREAST CANCER THERAPEUTIC AGENT CONTAINING 5'-HYDROXY-5-NITRO-INDIRUBIN-3'-OXIME AS ACTIVE INGREDIENT

This U.S. application claims priority to Korean Patent Application No. 10-2016-157929 filed on Nov. 25, 2016, the contents of which are incorporated herein by reference.

TECHNICAL FIELD

The present invention relates to a breast cancer therapeutic agent containing 5'-hydroxy-5-nitro-indirubin-3'-oxime as active ingredient. More particularly, this invention relates to a breast cancer therapeutic agent containing 5'-hydroxy-5-nitro-indirubin-3'-oxime as cyclin-dependent kinase (CDK) inhibitor, wherein said breast cancer is triple negative breast cancer (TNBC) and/or an estrogen receptor (ER) positive breast cancer including the tamoxifen-resistant estrogen receptor (ER) positive breast cancer.

DESCRIPTION OF PRIOR ART

Cyclin-dependent kinases (CDKs), belong to a group of serine/threonine kinases involved in the regulation of cell cycle progression, neuronal function, differentiation and apoptosis. Their activity is tightly regulated by multiple mechanisms including binding to corresponding cyclins, of which level of expression oscillates throughout the different phases of the cell cycle.

Different CDK/cyclin complexes are activated during each cell cycle step through G1, S, G2, M phases. Sequential phosphorylation of the retinoblastoma protein (pRb) by CDK4/cyclin D, CDK6/cyclin D in early G1 phase and CDK2/cyclin E in late G1 phase causes the release of the E2F, proteins of transcription factor. In turn, E2F proteins lead to transcriptional activation of a set of genes required for entry into S-phase of the cell cycle.

CDK2 is subsequently activated by cyclin A during the late stages of DNA replication, S-phase, and promotes appropriately timed deactivation of E2F to prevent apoptosis triggered by persistent E2F activity. Finally, CDK1 in complex with cyclin A or B is thought to have roles in regulating the G2/M checkpoint and driving cells through mitosis.

In addition to the cell cycle control, other roles have been determined for CDK2, 7, 8 and 9. For example, CDK2/Cyclin E is important to the p53 mediated DNA damage response pathway and CDK7, 8 and 9 are involved in the regulation of transcription initiation and elongation through phosphorylation of RNA polymerase. Therefore, CDKs affect cell growth and survival through several different mechanisms and proper regulation of CDK activity is important to various cellular processes.

It has been recognized that deregulation of CDKs by abnormal high expression of cyclin such as cyclin D and cyclin E or mutation occurs in many human tumors. For example, the expression and catalytic activity of CDK2/cyclin E complexes are increased in colorectal, ovarian, breast, and/or prostate cancers and elevated expression of cyclin E in primary tumors has a correlation with poor survival rates for breast cancer patients. Abnormal expression of CDK1/cyclin B complexes has been also observed in some cases, prostate adenocarcinoma and lung cancer.

Although the previous report has shown that CDK2 may not be required for cell cycle progression and proliferation, the recent reports have suggested that melanocytes and hepatocytes may be dependent on CDK2 for proliferation and survival. Also, an investigation of simultaneous depletion of CDK1 and CDK2 has been reported to provide increased efficacy in anti-proliferation of tumor cell lines, compared with targeting either CDK1 or CDK2 alone. In addition, emerging evidences have indicated that certain tumor cells may require specific interphase CDKs for proliferation.

At present, a number of small-molecule CDK inhibitors have been currently under clinical trials. These inhibitors are flat, small heterocycles which involve the competition with ATP in the kinase ATP-binding site. Among them, flavopyridol has been the first CDK inhibitor to enter clinical evaluations. R-Roscovitine (a trisubstituted purine analogue) and BMS-387032 (aminothiazole) are selective for CDK2/cyclin E, dinaciclib (MK-7965, SCH-727965) is selective for CDK1, 2, 5 and 9.

All CDK inhibitors developed to date can be classified into two main groups: broad-range inhibitors, such as, xavopiridol, olomoucine, roscovitine, kenpaullone, SNS-032, AT7519, AG-024322, (S)-Roscovitine and R547 and specific inhibitors, such as, fascaplysin, ryuvidine, purvalanol A, NU2058, BML-259, SU 9516, palbociclib (PD 0332991) and P-276-00.

Breast cancer is a worldwide health concern. Significant advances have been made in our understanding of this malignancy and several molecular subtypes of breast cancer have been characterized. This molecular understanding has paved the way for the development of new agents that target pathogenic molecular alterations that drive tumor cell growth. Ubiquitous to all cancer types is abnormal proliferation with dys-regulation of normal cell cycle control. For this reason, inhibitors of key cell cycle regulators are attractive targets for novel cancer therapeutics.

Under normal control, the cell cycle functions as a tightly regulated and predictable process consisting of several distinct phases: G0 (quiescence) followed by G1 (pre-DNA synthesis), S (DNA synthesis), G2 (pre-division) and M (cell division). The careful regulation of this system is of fundamental importance, and dys-regulation can result in several disease processes including cancer. The progression from G1 to S is a key checkpoint in protecting the cell from abnormal replication.

Several studies have identified alterations of cell cycle regulators in human breast cancer and provide a rationale for a potential therapeutic role for CDK4/6 inhibition in this tumor type. Amplification of the cyclin D1 gene has been identified in 15~20% of human breast cancers, while overexpression of the protein has been demonstrated in a higher percentage.

The prognostic significance of cyclin D1 overexpression is not clear; some studies suggest it is a dominant oncogene associated with poor clinical outcomes, while other studies suggest it is associated with a more indolent, estrogen receptor (ER)-positive phenotype.

In addition, studies have associated cyclin D amplification with resistance to tamoxifen. While the interaction between CDK4/6 and cyclin D1 suggests their interdependence, cyclin D1 has been found to function independently of CDK4/6 in supporting proliferation by directly activating ER.

Further, loss of function of pRb has been described in 20~35% of breast cancers. Recent data from a clinical trial with palbociclib in combination with letrozole has shown a CDK 4/6 inhibitor, palbociclib, plays a critical role to improve progression free survival in ER positive metastatic or advanced breast cancer.

On the other hand, dinaciclib (SCH-727965), one of CDK inhibitors, has been evaluating in clinical trials for various cancer indications, especially advanced breast cancer. The mechanisms of action have been considered as cyclin-dependent kinase inhibitor to interact with the acetyl-lysine recognition site of bromo-domains as well as to inhibit the unfolded protein response through a CDK1 and CDK5-dependent mechanism.

Indirubin and its derivatives having a bis-indole scaffold have been investigated with considerable interests as potent inhibitors targeting important protein kinases such as CDK, GSK-3β, and aurora kinases.

In U.S. Pat. No. 8,859,783 B2 'Indirubin-3'-oxime derivatives as potent cyclin dependent kinase inhibitors', the inventors of present invention have already disclosed indirubin-3'-oxime derivatives as cyclin-dependent kinase inhibitors. Further, it has been also disclosed that such cyclin-dependent kinase inhibitors have excellent anticancer activities against human lung cancer cell, human fibro sarcoma cell, human colon cancer cell, human leukemia cell, human stomach cancer cell, human nasopharyngeal cancer cell and/or human breast cancer cell.

In this U.S. patent disclosure, following indirubin-3'-oxime derivatives represented by Formula 1 have been disclosed.

Formula 1 wherein
i) $R_1$ is OH and $R_2$ is $NO_2$;
ii) $R_1$ is F and $R_2$ is $NO_2$;
iii) $R_1$ is OH and $R_2$ is Cl; or
iv) $R_1$ is OH and $R_2$ is F.

Among said indirubin-3'-oxime derivatives, the inventors of present invention have selected the optimal compound having excellent anticancer activity with minimum toxicity, which is 5'-hydroxy-5-nitro-indirubin-3'-oxime compound. This compound corresponds to the compound of Formula 1, wherein $R_1$ is OH and $R_2$ is $NO_2$. In this specification, this compound is, hereinafter, called as AGM-130.

Chemical name (IUPAC) of AGM-130 is (2'Z 3'E)-5'-hydroxy-5-nitro indirubin oxime. It is practically insoluble in water and soluble in DMF and DMSO and very difficult to dissolve in ethanol and acetone. For the practical formulation of injectable aqueous solution, AGM-130 in PEG300 solution is diluted with 0.1 N $Na_2CO_3$ in saline solution to 70% aqueous solution with final concentration of 3.75 mg/mL.

Preclinical studies indicate that AGM-130 is a highly selective CDK inhibitor, which effectively inhibits CDKs signaling in tumors. AGM-130 exhibited marked inhibitory activity on the growth of human tumor cell lines in vitro and of tumor xenografts. Further, AGM-130 frequently led to complete regressions of established tumors.

Previously, the inventors of present invention tried to measure the anticancer activity of 5'-hydroxy-5-nitro-indirubin-3'-oxime compound (AGM-130) against Imatinib-resistant chronic myeloid leukemia (CML) cells. Further, we found that this compound efficiently decreases the viability of Imatinib-resistant K562 cells in vitro and in vivo systems. These results have been disclosed in *Leukemia Research* vol. 37 pp. 427-433 (2013). However, we recently found that AGM-130 compound cannot be available as a drug for the treatment of CML, because the safety of AGM-130 compound cannot be fully guaranteed if it is applied to CML.

Subsequently, the inventors of present invention tried to measure the anticancer activity of 5'-hydroxy-5-nitro-indirubin-3'-oxime compound (AGM-130) against non-small cell lung cancer. Accordingly, we found that AGM-130 compound significantly inhibits the proliferation and arrests the cell cycle of G2/M phase against A549 human non-small cell lung cancer cells. It was also found that the protein levels of released Cytochrome C, Bax, cleaved caspases and PARP may increase. Further, in vivo tumor xenograft model, AGM-130 dose-dependently suppresses transplanted A549 cell tumor growth.

Further, these results have been disclosed in *European Journal of Pharmaceutical Sciences* vol. 79 pp. 122-131 (2015). However, we recently found that AGM-130 compound cannot be available as a drug for the treatment of non-small cell lung cancer, because the toxicity of AGM-130 compound cannot be fully guaranteed if it is applied to non-small cell lung cancer.

Therefore, the inventors of present invention have repeated in vitro and in vivo test to find out the optimally applied anticancer activity of AGM-130 compound against various kinds of cancer cell lines. Finally, the inventors of present invention have found that 5'-hydroxy-5-nitro-indirubin-3'-oxime compound (AGM-130) as cyclin-dependent kinase (CDK) inhibitor can be available as a drug for the treatment of triple negative breast cancer (TNBC) and/or an estrogen receptor (ER) positive breast cancer including the tamoxifen-resistant estrogen receptor (ER) positive breast cancer, because AGM-130 compound shows the optimal anticancer activity having the lowest toxicity if it is applied to these specific breast cancers.

Problem to be Solved

The problem to be solved is to find out the optimally applied anticancer activity of AGM-130 compound, by repeated in vitro and in vivo test against various kinds of cancer cell lines. Further, 5'-hydroxy-5-nitro-indirubin-3'-oxime compound (AGM-130) as cyclin-dependent kinase (CDK) inhibitor has been tried if it is available as a drug for the treatment of triple negative breast cancer (TNBC) and/or an estrogen receptor (ER) positive breast cancer including the tamoxifen-resistant estrogen receptor (ER) positive breast cancer.

Means for Solving the Problem

The object of the present invention is to provide a breast cancer therapeutic agent containing 5'-hydroxy-5-nitro-indirubin-3'-oxime as cyclin-dependent kinase (CDK) inhibitor as active ingredient, wherein said breast cancer is a triple negative breast cancer (TNBC) and/or an estrogen receptor (ER) positive breast cancer.

Further, said triple negative breast cancer (TNBC) is characterized in that the gene expressions of estrogen receptor (ER), progesterone receptor (PR) and/or Her2/neu receptor are silent.

Further, said estrogen receptor (ER) positive breast cancer includes a tamoxifen-resistant estrogen receptor (ER) positive breast cancer.

Further, said 5'-hydroxy-5-nitro-indirubin-3'-oxime inhibits the growth of cancer cells by arresting the G2/M phase in the cell cycle as well as remarkably reducing the cyclin B1 expression involved in G2/M phase in the breast cancer.

Further, said 5'-hydroxy-5-nitro-indirubin-3'-oxime inhibits the growth of cancer cells by mitochondria-dependent apoptosis.

Advantageous Effect

The advantageous effect of present invention is to provide the optimally applied anticancer activity of AGM-130 compound. Further, 5'-hydroxy-5-nitro-indirubin-3'-oxime compound (AGM-130) as cyclin-dependent kinase (CDK) inhibitor has been provided as an optimal drug for the treatment of triple negative breast cancer (TNBC) and/or an estrogen receptor (ER) positive breast cancer including the tamoxifen-resistant estrogen receptor (ER) positive breast cancer.

PREFERRED EMBODIMENT OF INVENTION

The present invention relates to a breast cancer therapeutic agent containing 5'-hydroxy-5-nitro-indirubin-3'-oxime as cyclin-dependent kinase (CDK) inhibitor as active ingredient, wherein said breast cancer is triple negative breast cancer (TNBC) and/or an estrogen receptor (ER) positive breast cancer including the tamoxifen-resistant estrogen receptor (ER) positive breast cancer.

The present invention can be explained more concretely as follows.

We have tried in vitro anticancer activity tests of AGM-130 compound against 60 kinds of cancer cell lines afforded by NCI. The inhibition of cancer cell growth has been measured using 10 µM of AGM-130 compound.

The in vitro results of inhibition of cell growth against 60 kinds of cancer cell lines have been shown as the growth percent. If the growth percent of cancer cells is 100%, it means that there has been no inhibition of cancer cell growth. If the growth percent is 0%, it means that no further growth of cancer cells occurs, which is an ideal case. On the other hand, if the growth percent is less than 0%, it means the anti-cancer agent shows higher lethality required for the inhibition of cell growth due to its high toxicity.

The results have been shown in Table 1.

TABLE 1

| Cell line | | Growth percent, % | | | |
|---|---|---|---|---|---|
| Leukemia | CCRE-CEM<br>0.49<br>SR<br>0.38 | HL-60(TB)<br>3.67 | K-562<br>20.90 | MOLT-4<br>2.17 | RPMI-8226<br>−7.92 |
| Non-small cell lung cancer | A549/ATCC<br>10.64<br>NCI-H322M<br>7.21 | HOP-62<br>−9.77<br>NCI-H460<br>−28.47 | HOP-92<br>−3.09<br>NCI-H522<br>−79.07 | NCI-H226<br>−4.70 | NCI-H23<br>3.19 |
| Colorectal cancer | COLO 205<br>65.80<br>KM12<br>−32.96 | HCC-2998<br>8.93<br>SW-620<br>3.18 | HCT-116<br>2.29 | HCT-15<br>10.28 | HT29<br>69.21 |
| CNS cancer | SF-268<br>6.50<br>U251<br>0.60 | SF-295<br>20.93 | SF-539<br>−34.15 | SNB-19<br>17.47 | SNB-75<br>−28.05 |
| Malignant melanoma | LOX IMVI<br>−32.44<br>SK-MEL-28<br>−11.04 | MALME-3M<br>11.73<br>SK-MEL-4<br>−40.95 | M14<br>11.37<br>UACC-257<br>9.29 | MDA-MB-435<br>9.35<br>UACC-62<br>−34.39 | SK-MEL-2<br>−55.01 |
| Ovarian cancer | IGROV1<br>6.36<br>NCI/ADR/RES<br>42.05 | OVCAR-3<br>4.31<br>SK-OV-3<br>−9.52 | OVCAR-4<br>19.65 | OVCAR-5<br>11.33 | OVCAR-8<br>7.71 |
| Renal cell carcinoma | 786-0<br>4.21<br>TK-10<br>49.89 | A498<br>−24.52<br>UO-31<br>−1.14 | ACHN<br>−25.79 | CAKI-1<br>−14.28 | SN12C<br>23.68 |
| Prostate cancer | PC-3<br>2.12 | DU-145<br>6.72 | | | |
| Breast cancer | MCF-7<br>2.75 | MDA-MB-231<br>25.45 | HS 578T<br>1.21 | BT-549<br>4.59 | T-47D<br>16.80 |

In case of leukemia cell line, AGM-130 compound cannot be applied to RPMI-8226 cell line due to its high toxicity, while it shows the moderate inhibition of cell growth regarding other cell lines. In case of non-small cell lung cancer, AGM-130 compound also cannot be applied to almost all cell lines due to its high toxicity. Further, in case of central nervous system (CNS) cancer, AGM-130 compound cannot be applied to SF-539, SNB-75 cell lines due to its high toxicity.

In case of malignant melanoma, AGM-130 compound cannot be available to almost all cell lines due to its high toxicity. Further, in case of ovarian cancer and renal cell carcinoma, AGM-130 compound cannot be available to certain kinds of cell lines due to its high toxicity.

On the other hand, AGM-130 compound shows excellent anticancer activities against colorectal cancer cell lines except KM12 colorectal cancer cell line. In case of HCT-116 cancer cell line, the volume of tumor has been reduced in xenografted model. However, it cannot be interpreted as significant reduction of tumor volume.

However, in case of the breast cancer, AGM-130 compound shows excellent anticancer activities having the lowest toxicity against all cell lines, that are, MCF-7 cell line, MDA-MB-231 triple negative breast cancer cell line, HS 578T, BT-549 and T-47D cancer cell line.

To confirm the anti-proliferative activity of AGM-130 against breast cancer cell lines, we have evaluated in 18 different kinds of breast cancer cell lines. As the results, 4 types of Her2 positive breast cancer cell lines showed relatively insensitive with $IC_{50}$ values higher than 3 μM, whereas the growth of 3 types of ER positive and 7 of 10 types of triple negative cell lines was potently inhibited with $IC_{50}$ values below 1 μM.

Further, we have investigated the cell cycles of MDA-MB-231 breast cancer cell line through Flow cytometry analysis. As a result, decreased G1 phase and increased G2/M phase have been observed upon treatment of AGM-130. Further, the western blot showed that cyclin B1 expression involved in G2/M phase was remarkably reduced, suggesting that G2/M phase arrest was induced by AGM-130.

Further, we have examined the apoptotic body stained with DAPI using a fluorescence microscope to investigate the induction of apoptosis by AGM-130. As a result, AGM-130 inhibited cancer cell proliferation under the mechanism of mitochondria-dependent apoptosis.

Further, we have analyzed the secretion of LDH (Lactate dehydrogenase) enzyme to media as a representative necrosis biomarker. Consequently, apoptosis and necrosis have been induced at the same time by AGM-130.

Then, we have tried to in vivo inhibition of breast cancer cell growth according to breast cancer xenografted model of the mouse, especially the triple negative breast cancer and the tamoxifen resistant breast cancer xenografted model.

From the breast cancer xenografted model, we have confirmed that AGM-130 compound dose dependently inhibits the growth of cancer cells of MDA-MB-231 triple negative breast cancer and/or TAMR-MCF-7 tamoxifen resistant breast cancer.

The triple negative breast cancer is characterized in the absence of estrogen receptor (ER), progesterone receptor (PR) and HER-2 receptor in cancer cells. Therefore, receptor target therapy cannot be available for treating this triple negative breast cancer.

Until now, the anticancer agent for specifically treating the triple negative breast cancer or tamoxifen resistant estrogen receptor positive breast cancer has not been developed. Therefore, the conventional anticancer agent has been administered in a high dose for treating these breast cancers. However, the introduction of AGM-130 compound can be the selective and optimal therapeutic agent for these breast cancers. The mechanism for CDK inhibitor of AGM-130 compound has been considered by arresting the G2/M phase in the cancer cell cycle by inhibiting the cyclin-dependent kinase signal.

The AGM-130 compound of present invention can be formulated with at least one of pharmaceutically acceptable carriers or diluents. The proper pharmaceutically acceptable carrier or diluent can be at least one selected from calcium phosphate, magnesium stearate, talc, monosaccharide, disaccharide, starch, gelatin, cellulose, methylcellulose, sodium carboxymethylcellulose, dextrose, hydroxypropyl-β-cyclodextrin and/or polyvinylpyrrolidone.

The therapeutic dose of AGM-130 compound for a subject may be 0.1~100 mg/kg-weight in a day. The preferred dose of AGM-130 compound may be 0.5~30 mg/kg-weight in a day.

The AGM-130 compound may also be administered orally, parenterally, sublingually, rectally or topically to the subject. The dosage formulation can include a non-toxic pharmaceutically acceptable carrier, adjuvant and/or vehicle.

It is also preferred that the AGM-130 compound can be formulated for injectable preparation having aqueous or inaqueous solution or suspension. In this injectable preparation, suitable dispersing agent, wetting agent and/or suspending agent can be included.

The injectable preparation may be administered in the form of a liposome. Liposome is typically derived from phospholipid or lipid material, which includes single or multi-layer hydrated lipoid suspended and dispersed in an aqueous medium.

Further, the AGM-130 compound may be administered alone or in combination with other anticancer drugs. Examples of the anticancer drugs which can be administered are at least one selected from irinotecan, topotecan, gemcitabine, glivec, herceptin, 5-fluorouracil, leucovorin, carboplatin, cisplatin, taxane, tezacitabine, cyclophosphamide, vinca-alkaloid, imatinib, anthracycline, rituximab, trastuzumab and/or topoisomerase I inhibitor.

The present invention can be explained more concretely by following examples. However, the scope of present invention shall not be interpreted by limiting following examples.

(Example 1) Anticancer Activity Test in MDA-MB-231 Triple Negative Breast Cancer Xenografted Model (Intraperitoneally Injected)

After implanting MDA-MB-231 triple negative breast cancer cells to the nude mouse, the tumor has been grown to the 200 $mm^3$ volume. Then, 10/20/40 mg/kg doses of AGM-130 compound have been administered to the mouse intraperitoneally twice a week. The tumor growth has been observed for 27 days.

Figure 1:
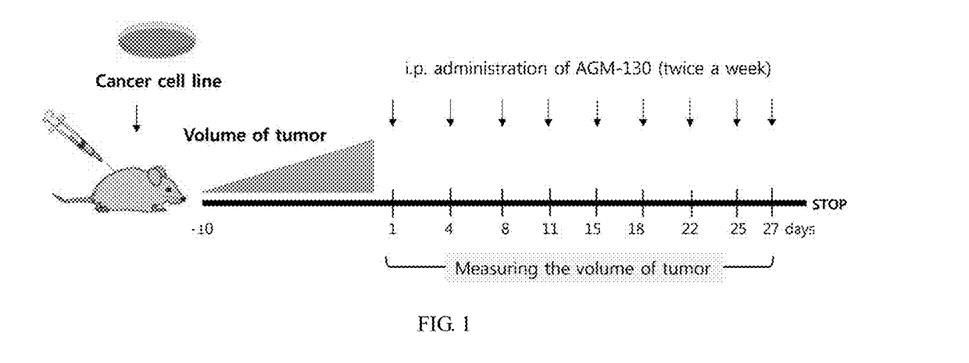
FIG. 1 shows a schematic view of triple negative breast cancer (MDA-MB-231) xenografted model design for measuring the anticancer activities of AGM-130 compound of the present invention, wherein AGM-130 compound is intraperitoneally injected to the mouse.

FIG. 1 shows a schematic view of MDA-MB-231 triple negative breast cancer xenografted model design for measuring the anticancer activities of AGM-130 compound of the present invention, wherein AGM-130 compound is intraperitoneally administered to the mouse.

As shown in FIG. 1, MDA-MB-231 triple negative breast cancer cells have been inoculated to the mouse. After 10 days, 10/20/40 mg/kg doses of AGM-130 compound have been administered to the mouse intraperitoneally twice a week. The tumor volume and shape in the nude mouse have been observed for 27 days.

Figure 2:
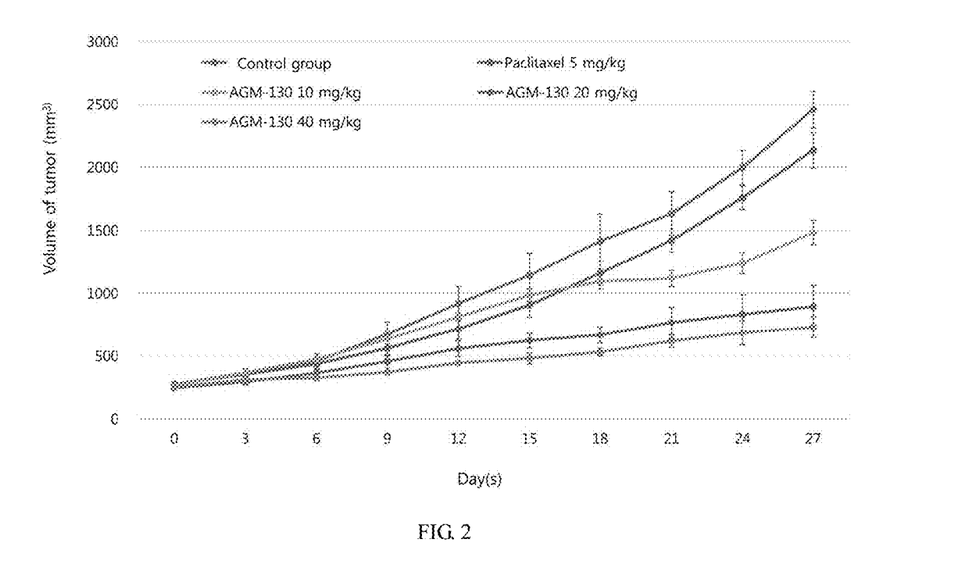
FIG. 2 shows a graph indicating that the volume of tumor is dose-dependently reduced in the triple negative breast cancer (MDA-MB-231) xenografted model, wherein AGM-130 compound is intraperitoneally administered to the mouse.

FIG. 2 shows a graph indicating that the volume of tumor is dose-dependently reduced in MDA-MB-231 triple negative breast cancer xenografted model, wherein AGM-130 compound is intraperitoneally administered to the mouse. As shown in FIG. 2, the volume of tumor inoculated and grown by MDA-MB-231 breast cancer cell has been reduced dose-dependently after administering AGM-130 compound.

In this experiment, as a control group, paclitaxel (5 mg/kg) has been administered to the mouse. The administration of AGM-130 compound results in about 14% tumor volume reduction compared to that of control group. It means that AGM-130 compound shows better anticancer activities against breast cancer rather than paclitaxel.

The table 2 shows the anticancer activity results of AGM-130 compound in the MDA-MB-231 triple negative breast cancer xenografted model. After intraperitoneally administering the doses (10/20/40 mg/kg) of AGM-130 compound to the nude mouse, the volumes of tumors have been measured. As a control group, the volume of tumor in the nude mouse without administering AGM-130 compound has been employed.

TABLE 2

| | Mean ± S.E. | | | | |
| --- | --- | --- | --- | --- | --- |
| | | | AGM-130 group | | |
| day(s) | Control group | Paclitaxel | 10 mg/kg | 20 mg/kg | 40 mg/kg |
| 0 | 274.8 ± 12.7 | 277.1 ± 16.2 | 268.0 ± 6.1 | 248.0 ± 11.0 | 253.1 ± 8.5 |
| 3 | 369.6 ± 28.1 | 354.3 ± 6.3 | 369.7 ± 5.0 | 295.4 ± 22.0 | 313.3 ± 9.7 |
| 6 | 458.1 ± 52.9 | 437.9 ± 20.8 | 474.3 ± 6.6 | 364.9 ± 23.5 | 327.5 ± 19.1 |
| 9 | 672.8 ± 89.6 | 562.4 ± 53.4 | 634.9 ± 36.2 | 457.4 ± 47.3 | 372.4 ± 8.3 |
| 12 | 919.5 ± 121.8 | 716.8 ± 72.9 | 813.5 ± 29.0 | 559.5 ± 56.2 | 444.8 ± 7.3 |
| 15 | 1144.5 ± 156.6 | 906.2 ± 88.2 | 985.6 ± 44.8 | 623.4 ± 51.5 | 481.9 ± 39.1 |
| 18 | 1414.7 ± 195.4 | 1161.2 ± 86.4 | 1095.7 ± 54.2 | 668.5 ± 56.8 | 532.7 ± 27.6 |
| 21 | 1634.7 ± 154.2 | 1421.7 ± 82.6 | 1119.8 ± 57.7 | 767.2 ± 106.7 | 620.1 ± 45.2 |
| 24 | 1999.4 ± 122.0 | 1760.2 ± 83.8 | 1242.1 ± 76.0 | 833.1 ± 139.7 | 686.2 ± 85.6 |
| 27 | 2459.6 ± 131.1 | 2136.0 ± 125.9 | 1484.9 ± 86.8 | 894.2 ± 151.6 | 730.8 ± 73.9 |

Figure 3:
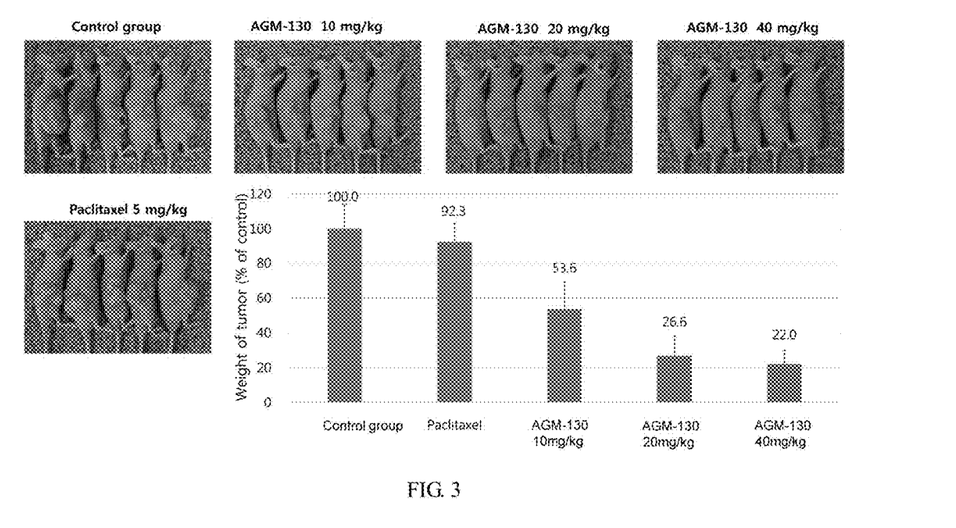
FIG. 3 shows a photo and a graph indicating the dose-dependent anticancer activity in the triple negative breast cancer (MDA-MB-231) xenografted model, wherein AGM-130 compound is intraperitoneally administered to the mouse.

FIG. 3 shows a photo and a graph indicating the dose-dependent anticancer activity in the MDA-MB-231 triple negative breast cancer xenografted model, wherein AGM-130 compound is intraperitoneally administered to the mouse.

As shown in Table 2, the administration of 10 mg/kg dose of AGM-130 compound results in about 40% tumor volume reduction compared to that of control group. Further, the administration of 20 mg/kg dose of AGM-130 compound results in about 64% tumor volume reduction compared to that of control group. Especially, the administration of 40 mg/kg dose of AGM-130 compound results in about 70% tumor volume reduction compared to that of control group.

(Example 2) Anticancer Activity Test in MDA-MB-231 Triple Negative Breast Cancer Xenografted Model (Intravenously Injected)

After implanting MDA-MB-231 triple negative breast cancer cells to the nude mouse, the tumor has been grown to the 200 mm$^3$ volume. Then, 3/7/14 mg/kg doses of AGM-130 compound have been administered to the mouse intravenously once a week. The tumor growth has been observed for 24 days.

Figure 4:
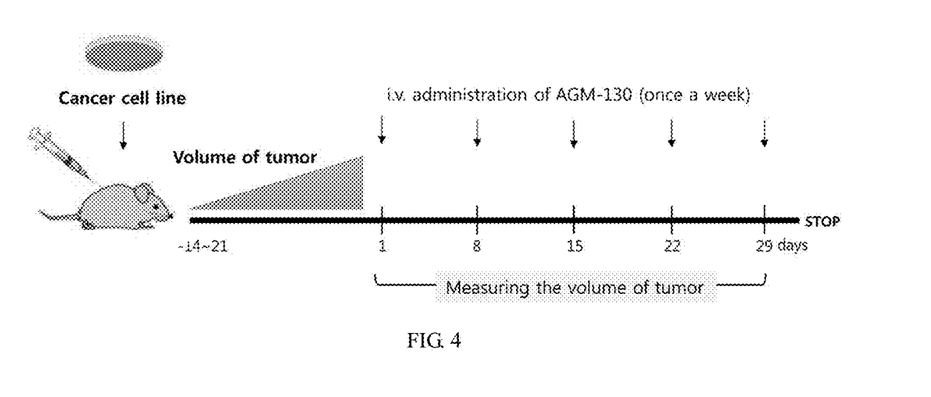
FIG. 4 shows a schematic view of triple negative breast cancer (MDA-MB-231) xenografted model design for measuring the anticancer activities of AGM-130 compound of the present invention, wherein AGM-130 compound is intravenously administered to the mouse.

FIG. 4 shows a schematic view of MDA-MB-231 triple negative breast cancer xenografted model design for measuring the anticancer activities of AGM-130 compound of the present invention, wherein AGM-130 compound is intravenously administered to the mouse.

As shown in FIG. 4, MDA-MB-231 triple negative breast cancer cells have been inoculated to the mouse. After 10 days, 3/7/14 mg/kg doses of AGM-130 compound have been administered to the mouse intravenously once a week. The tumor volume and shape in the nude mouse have been observed for 24 days.

Figure 5:
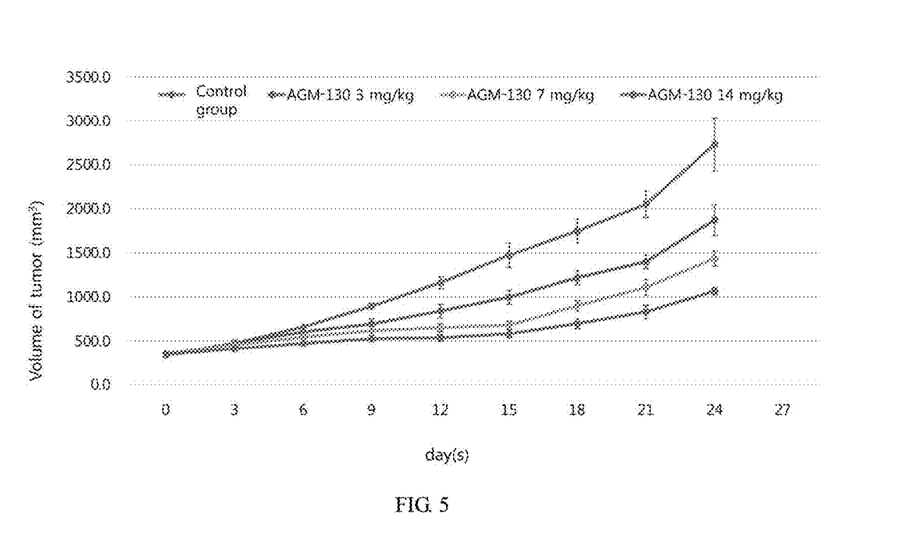
FIG. 5 shows a graph indicating that the volume of tumor is dose-dependently reduced in the triple negative breast cancer (MDA-MB-231) xenografted model, wherein AGM-130 compound is intravenously administered to the mouse.

FIG. 5 shows a graph indicating that the volume of tumor is dose-dependently reduced in the MDA-MB-231 triple negative breast cancer xenografted model, wherein AGM-130 compound is intravenously administered to the mouse.

As shown in FIG. 5, the volume of tumor inoculated and grown by MDA-MB-231 breast cancer cell has been reduced dose-dependently after administering AGM-130 compound.

The table 3 shows the anticancer activity results of AGM-130 compound in the MDA-MB-231 triple negative breast cancer xenografted model. After intravenously administering the doses (3/7/14 mg/kg) of AGM-130 compound to the nude mouse, the volumes of tumors have been measured. As a control group, the volume of tumor in the nude mouse without administering AGM-130 compound has been employed.

Figure 6:
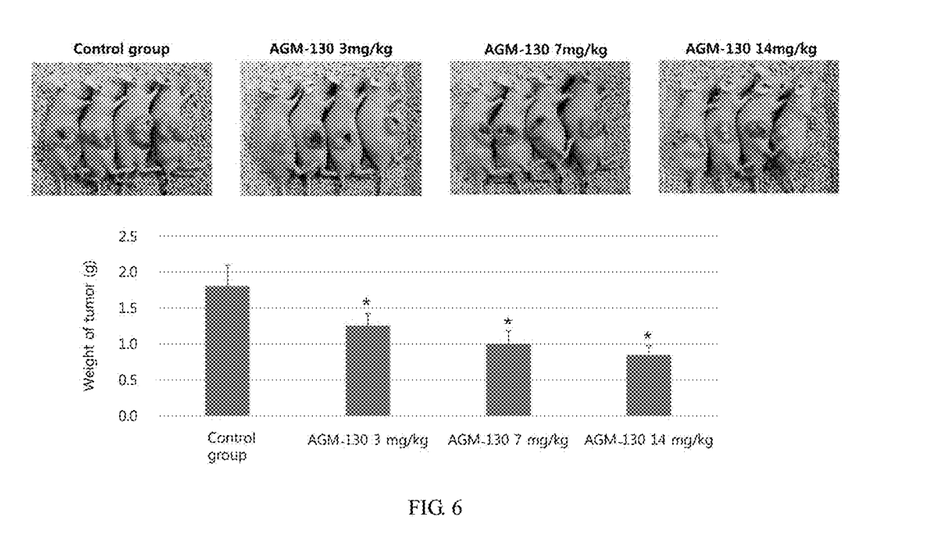
FIG. 6 shows a photo and a graph indicating that the weight of tumor is dose-dependently reduced in the triple negative breast cancer (MDA-MB-231) xenografted model, wherein AGM-130 compound is intravenously administered to the mouse.

FIG. 6 shows a graph indicating that the weight of tumor is dose-dependently reduced in the MDA-MB-231 triple negative breast cancer xenografted model, wherein AGM-130 compound is intravenously administered to the mouse.

As shown in Table 3, the administration of 3 mg/kg dose of AGM-130 compound results in about 31% tumor volume reduction compared to that of control group. Further, the administration of 7 mg/kg dose of AGM-130 compound results in about 47% tumor volume reduction compared to that of control group. Especially, the administration of 14 mg/kg dose of AGM-130 compound results in about 61% tumor volume reduction compared to that of control group.

(Example 3) Anticancer Activity Test in TAMR-MCF-7 Tamoxifen Resistant Breast Cancer Xenografted Model (Intraperitoneally Injected)

After implanting and growing TAMR-MCF-7 tamoxifen resistant breast cancer cells to the nude mouse, 10/40 mg/kg doses of AGM-130 compound have been administered to the mouse intraperitoneally twice a week. The tumor growth has been observed for 24 days.

Figure 7:
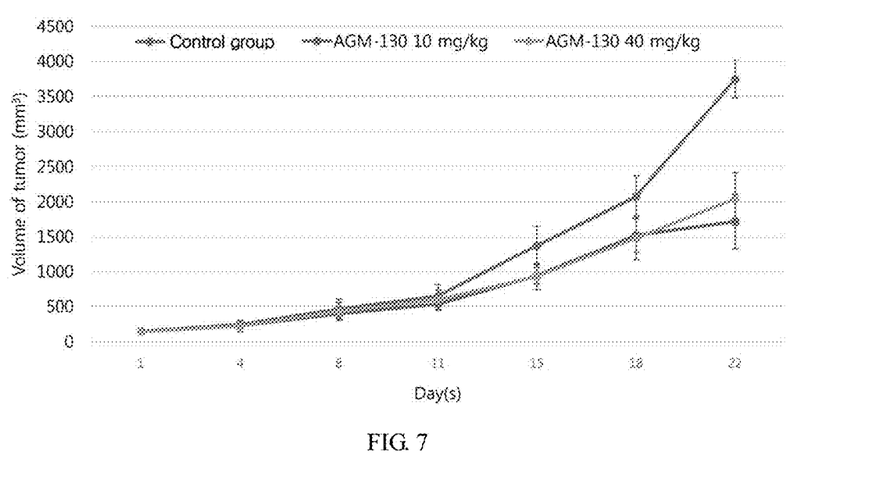
FIG. 7 shows a graph indicating that the volume of tumor is dose-dependently reduced in the tamoxifen-resistant breast cancer (TAMR-MCF-7) xenografted model, wherein AGM-130 compound is intraperitoneally administered to the mouse.

FIG. 7 shows a graph indicating that the volume of tumor is dose-dependently reduced in the TAMR-MCF-7 tamoxifen-resistant breast cancer xenografted model, wherein AGM-130 compound is intraperitoneally administered to the mouse.

As shown in FIG. 7, the administration of 10 mg/kg dose of AGM-130 compound results in about 54% tumor volume reduction compared to that of control group. Further, the administration of 40 mg/kg dose of AGM-130 compound results in about 45% tumor volume reduction compared to that of control group.

Further, the weight of mouse administered with 10/40 mg/kg dose of AGM-130 compound has changed significantly compared to that of control group.

Figure 8A:
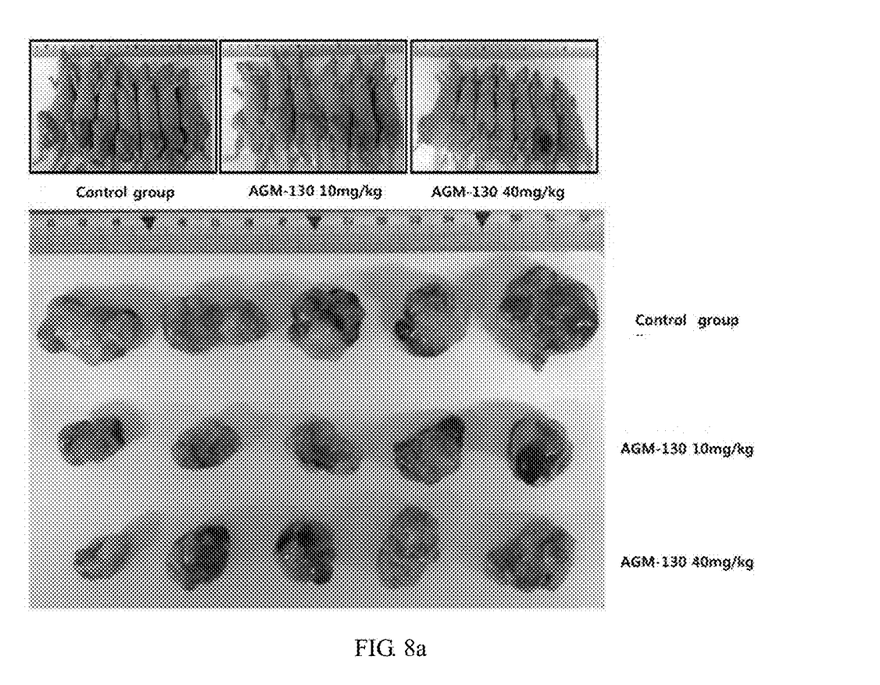
FIG. 8a shows a photo indicating the dose-dependent anticancer activity in the tamoxifen-resistant breast cancer (TAMR-MCF-7) xenografted model, wherein AGM-130 compound is intraperitoneally administered to the mouse.

FIG. 8a shows a photo indicating the dose-dependent anticancer activity in the TAMR-MCF-7 tamoxifen-resistant breast cancer xenografted model, wherein AGM-130 compound is intraperitoneally administered d to the mouse.

Figure 8B:
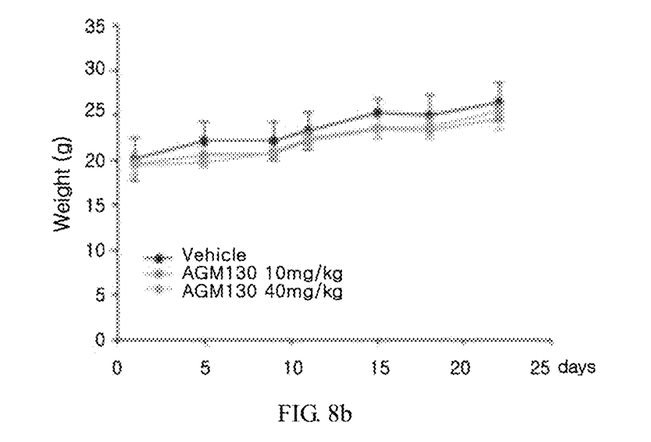
FIG. 8b shows a graph indicating that the volume of tumor is dose-dependently reduced in the tamoxifen-resistant breast cancer (TAMR-MCF-7) xenografted model, wherein AGM-130 compound is intraperitoneally administered to the mouse.

FIG. 8b shows a graph indicating that the volume of tumor is dose-dependently reduced in the TAMR-MCF-7 tamoxifen-resistant breast cancer xenografted model, wherein AGM-130 compound is intraperitoneally administered to the mouse.

Ah shown in FIG. 8, the reduction of tumor volume has been significantly observed in both 10 mg/kg dose of AGM-130 administered mouse and 40 mg/kg dose of AGM-130 administered mouse.

Figure 9:
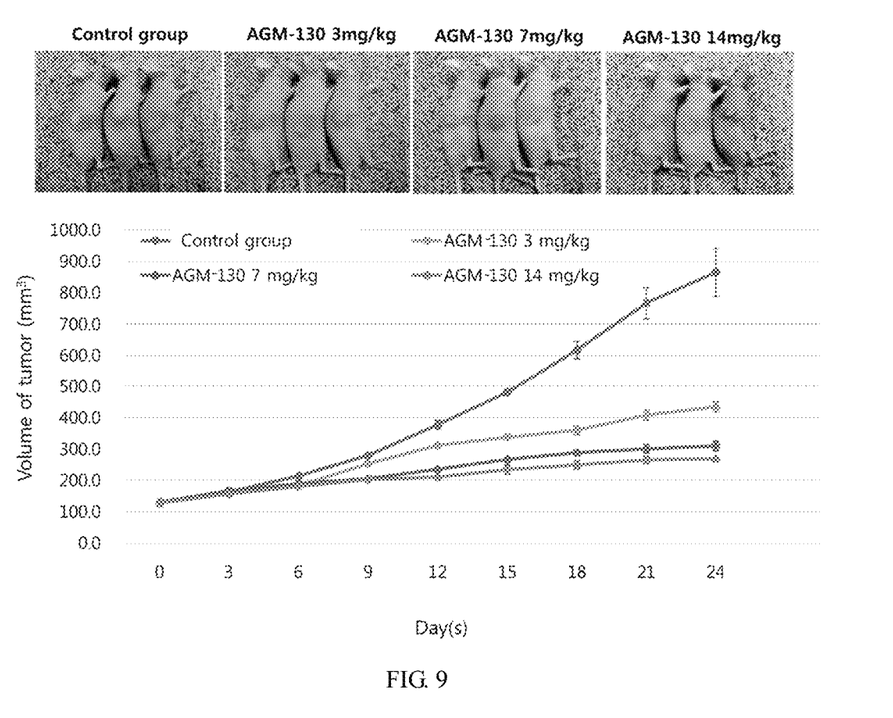
FIG. 9 shows a photo and a graph indicating that the volume of tumor is dose-dependently reduced in the MCF-7 ER positive breast cancer xenografted model, wherein AGM-130 compound is intravenously administered to the mouse.

FIG. 9 shows a photo and a graph indicating that the volume of tumor is dose-dependently reduced in the MCF-7

TABLE 3

| | | AGM-130 group | | |
| --- | --- | --- | --- | --- |
| day(s) | Control group | 3 mg/kg | 7 mg/kg | 14 mg/kg |
| 0 | 337.4 ± 20.0 | 341.5 ± 14.4 | 355.4 ± 10.7 | 342.1 ± 20.7 |
| 3 | 474.2 ± 37.2 | 474.6 ± 26.4 | 451.9 ± 10.2 | 408.5 ± 10.3 |
| 6 | 658.3 ± 18.4 | 602.5 ± 44.1 | 543.4 ± 10.9 | 470.8 ± 20.4 |
| 9 | 894.1 ± 34.6 | 693.1 ± 61.0 | 615.5 ± 19.0 | 525.4 ± 35.6 |
| 12 | 1160.1 ± 68.8 | 838.0 ± 79.9 | 651.0 ± 47.1 | 535.3 ± 39.0 |
| 15 | 1472.2 ± 136.8 | 996.9 ± 79.9 | 677.9 ± 46.7 | 581.5 ± 44.8 |
| 18 | 1746.0 ± 136.6 | 1217.5 ± 81.8 | 899.6 ± 59.6 | 696.1 ± 54.6 |
| 21 | 2051.6 ± 150.4 | 1398.0 ± 78.1 | 1108.9 ± 88.1 | 831.0 ± 75.1 |
| 24 | 2730.5 ± 302.9 | 1871.4 ± 175.5 | 1436.1 ± 84.8 | 1064.3 ± 39.8 |

ER positive breast cancer xenografted model, wherein AGM-130 compound is intravenously administered to the mouse.

As shown in FIG. 9, MCF-7 ER positive breast cancer cells have been inoculated to the mouse. After 10 days, 3/7/14 mg/kg doses of AGM-130 compound have been administered to the mouse intravenously once a week. The tumor volume and shape in the nude mouse have been observed for 24 days.

The table 4 shows the anticancer activity results of AGM-130 compound in the MCF-7 breast cancer xenografted model. After intravenously administering the doses (3/7/14 mg/kg) of AGM-130 compound to the nude mouse, the volumes of tumors have been measured. As a control group, the volume of tumor in the nude mouse without administering AGM-130 compound has been employed.

TABLE 4

| day(s) | Control group | AGM-130 group | | |
|---|---|---|---|---|
| | | 3 mg/kg | 7 mg/kg | 14 mg/kg |
| 0 | 128.0 ± 13.5 | 131.9 ± 8.6 | 129.1 ± 3.8 | 127.8 ± 2.4 |
| 3 | 162.8 ± 12.7 | 167.5 ± 7.1 | 166.9 ± 7.4 | 156.8 ± 4.7 |
| 6 | 214.2 ± 50.0 | 182.3 ± 4.2 | 190.0 ± 6.3 | 180.6 ± 5.0 |
| 9 | 279.5 ± 1.1 | 253.3 ± 7.9 | 205.6 ± 11.4 | 202.9 ± 3.8 |
| 12 | 377.4 ± 16.4 | 311.9 ± 2.3 | 235.6 ± 7.1 | 210.6 ± 5.1 |
| 15 | 480.9 ± 11.8 | 337.5 ± 11.0 | 267.3 ± 9.4 | 234.7 ± 17.8 |
| 18 | 617.5 ± 32.6 | 359.8 ± 15.6 | 288.1 ± 6.2 | 249.4 ± 15.3 |
| 21 | 766.5 ± 57.5 | 408.2 ± 19.0 | 300.2 ± 15.4 | 264.8 ± 12.9 |
| 24 | 864.5 ± 87.9 | 434.5 ± 18.3 | 310.1 ± 18.2 | 268.7 ± 8.7 |

As shown in Table 4, the administration of 3 mg/kg dose of AGM-130 compound results in about 49% tumor volume reduction compared to that of control group. Further, the administration of 7 mg/kg dose of AGM-130 compound results in about 64% tumor volume reduction compared to that of control group. Especially, the administration of 14 mg/kg dose of AGM-130 compound results in about 69% tumor volume reduction compared to that of control group.

It means that the volume of tumor grown by MCF-7 breast cancer cells has been reduced dose-dependently after administering AGM-130 compound. Therefore, AGM-130 compound has been proved to be an effective therapeutics for treating ER positive breast cancer.

Therefore, it has been expected that AGM-130 compound of present invention can be an effective anticancer therapeutics for treating a triple negative breast cancer (TNBC) and/or an estrogen receptor (ER) positive breast cancer including the tamoxifen-resistant estrogen receptor (ER) positive breast cancer.

(Comparative Example 1) Anticancer Activity Test in KB Oral Cavity Cancer Xenografted Model (Intraperitoneally Injected)

The tumor has been grown after injecting KB oral cavity cancer cells ($10 \times 10^6$ cells/0.1 ml of non-serum matrigel medium) to the nude mouse. Then, 5/10/20 mg/kg doses of AGM-130 compound have been administered to the mouse intraperitoneally every other day. The tumor growth has been observed for 28 days.

Figure 10:
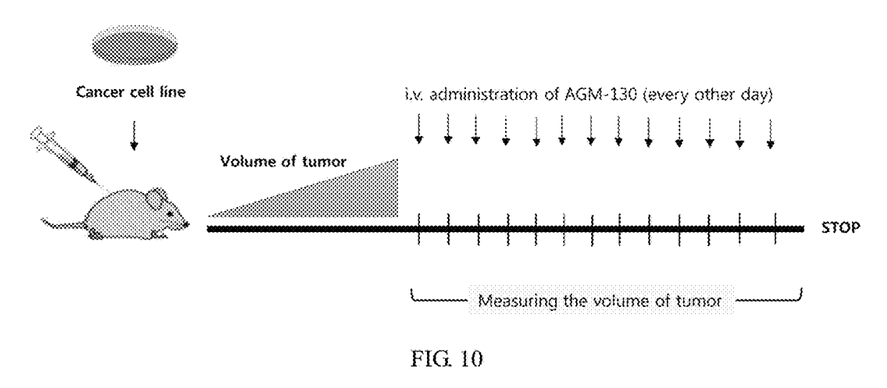
FIG. 10 shows a schematic view of the KB oral cavity cancer xenografted model design as a comparative example regarding the anticancer activities of AGM-130 compound, wherein AGM-130 compound is intraperitoneally administered to the mouse.

FIG. 10 shows a schematic view of the KB oral cavity cancer xenografted model design as a comparative example regarding the anticancer activities of AGM-130 compound, wherein AGM-130 compound is intraperitoneally administered to the mouse.

As shown in FIG. 10, KB oral cavity cancer cells have been inoculated to the mouse. After 10 days, 5/10/20 mg/kg doses of AGM-130 compound have been administered to the mouse intraperitoneally every other day. The tumor volume and shape in the nude mouse have been observed for 28 days.

Figure 11:
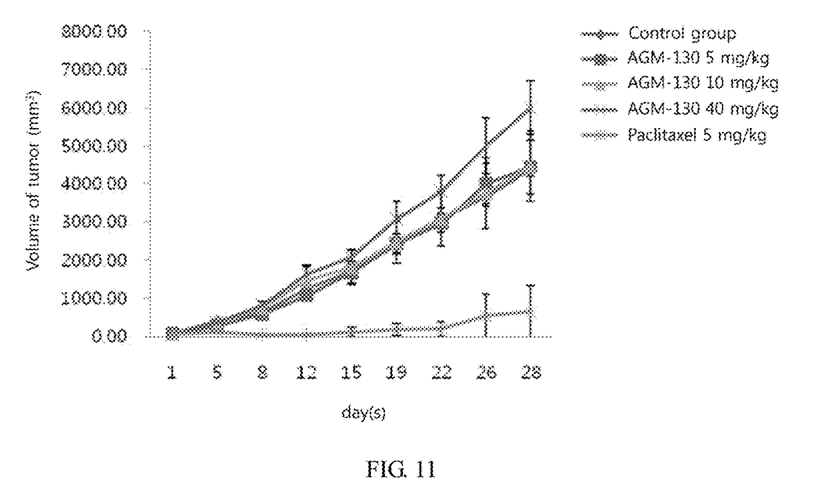
FIG. 11 shows a graph indicating how the volume of tumor is changed in the KB oral cavity cancer xenografted model as a comparative example, wherein AGM-130 compound is intraperitoneally administered to the mouse.

FIG. 11 shows a graph indicating how the volume of tumor is changed in the KB oral cavity cancer xenografted model as a comparative example, wherein AGM-130 compound is intraperitoneally administered to the mouse.

As shown in FIG. 11, the volume of tumor inoculated and grown by KB oral cavity cancer cells cannot be reduced significantly in a dose-dependent manner after administering AGM-130 compound.

In this experiment, as a positive control group, paclitaxel (10 mg/kg) has been administered to the mouse. The administration of AGM-130 compound cannot result in significant reduction of volume of tumor compared to that of paclitaxel.

(Comparative Example 2) Anticancer Activity Test in HCT-116 Colorectal Cancer Xenografted Model (Intraperitoneally Injected)

The tumor has been grown after injecting HCT-116 colorectal cancer cells ($10 \times 10^6$ cells/0.1 ml of non-serum matrigel medium) to the nude mouse. Then, 10 mg/kg dose of AGM-130 compound has been administered to the mouse intraperitoneally every other day. The tumor growth has been observed for 24 days.

Figure 12:
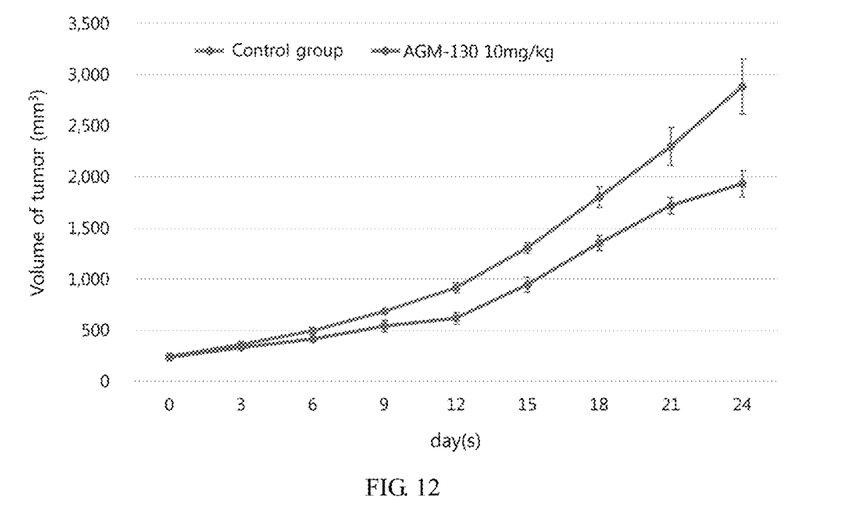
FIG. 12 shows a graph indicating how the volume of tumor is changed in the HCT-116 colorectal cancer xenografted model as a comparative example, wherein AGM-130 compound is intraperitoneally administered to the mouse.

FIG. 12 shows a graph indicating how the volume of tumor is changed in the HCT-116 colorectal cancer xenografted model as a comparative example, wherein AGM-130 compound is intraperitoneally administered to the mouse.

As shown in FIG. 12, HCT-116 colorectal cancer cells have been inoculated to the mouse. After 10 days, 10 mg/kg dose of AGM-130 compound has been administered to the mouse intraperitoneally every other day. The tumor volume and shape in the nude mouse have been observed for 24 days.

As shown in FIG. 12, the volume of tumor inoculated and grown by HCT-116 colorectal cancer cells cannot be reduced significantly in a dose-dependent manner after administering AGM-130 compound.

Figure 13:
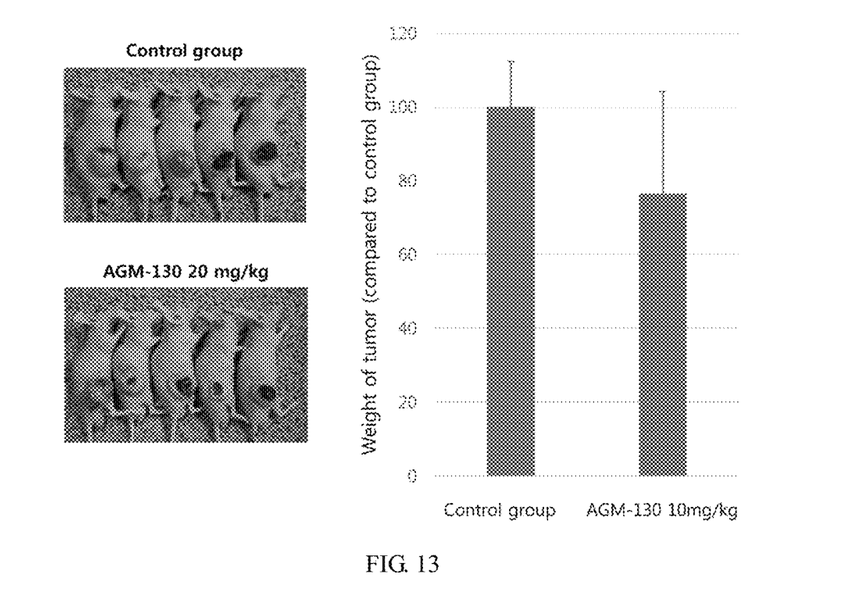
FIG. 13 shows a photo and a graph indicating how the volume and weight of tumor are changed in the HCT-116 colorectal cancer xenografted model as a comparative example, wherein AGM-130 compound is intraperitoneally administered to the mouse.

FIG. 13 shows a photo and a graph indicating how the volume and weight of tumor are changed in the HCT-116 colorectal cancer xenografted model as a comparative example, wherein AGM-130 compound is intraperitoneally administered to the mouse.

As shown in FIG. 13, the volume of tumor inoculated and grown by HCT-116 colorectal cancer cells cannot be reduced significantly in a dose-dependent manner after administering AGM-130 compound.

(Comparative Example 3) Anticancer Activity Test in A549 Lung Cancer Xenografted Model (Intraperitoneally Injected)

The tumor has been grown after injecting A549 lung cancer cells to the nude mouse. Then, 10/20/40 mg/kg doses of AGM-130 compound have been administered to the mouse intraperitoneally every other day. The tumor growth has been observed for 27 days.

Figure 14:
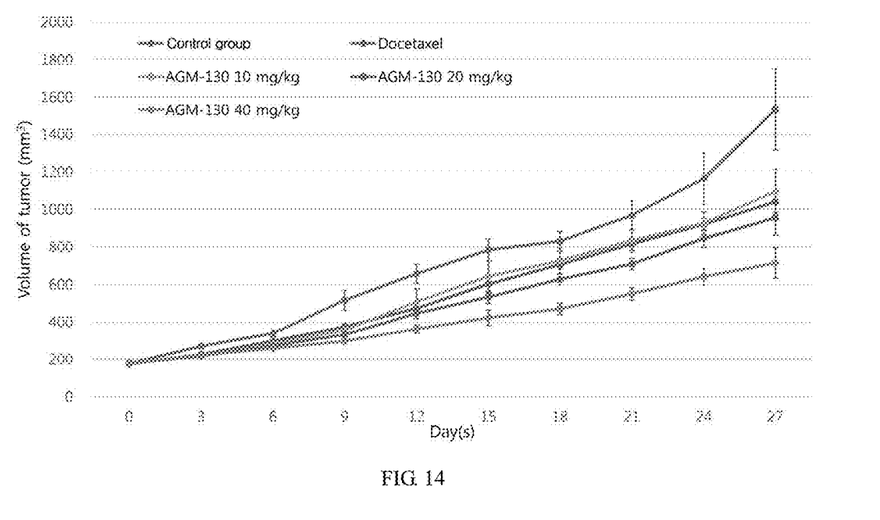
FIG. 14 shows a graph indicating how the volume of tumor is changed in the A549 lung cancer xenografted model as a comparative example, wherein AGM-130 compound is intraperitoneally administered to the mouse.

FIG. 14 shows a graph indicating how the volume of tumor is changed in the A549 lung cancer xenografted model as a comparative example, wherein AGM-130 compound is intraperitoneally administered to the mouse.

As shown in FIG. 14, the A549 lung cancer cells have been inoculated to the mouse. After 10 days, 10/20/40 mg/kg doses of AGM-130 compound have been administered to the mouse intraperitoneally every other day. The tumor volume and shape in the nude mouse have been observed for 27 days. As a positive control, docetaxel (5 mg/kg) has been administered.

As shown in FIG. 14, the volume of tumor grown by A549 lung cancer cells cannot be reduced significantly in a dose-dependent manner after administering AGM-130 compound. Further, the anticancer activity of AGM-130 compound seems to be similar to that of docetaxel.

Figure 15A:
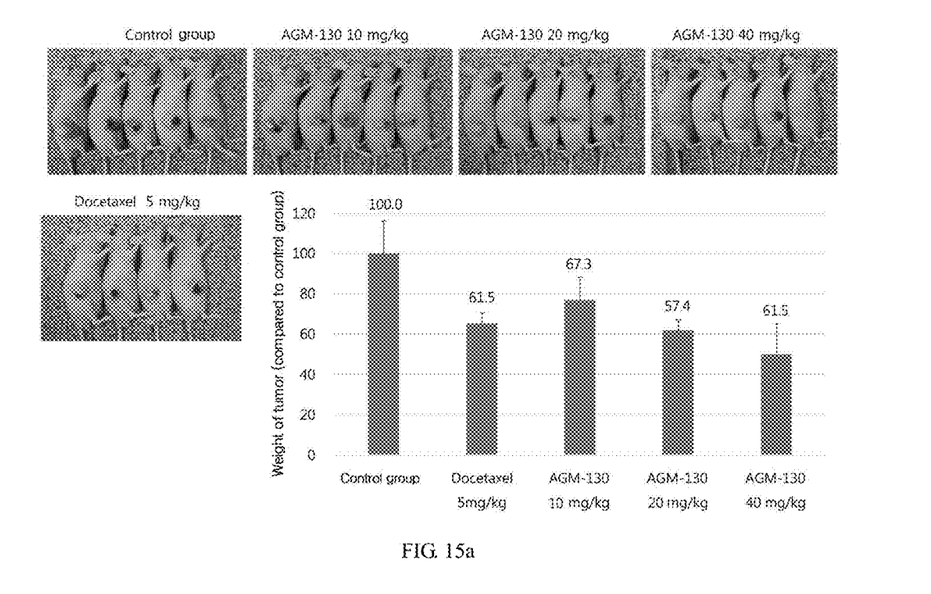
FIG. 15a shows a photo and a graph indicating how the weight of tumor is changed in the A549 lung cancer xenografted model as a comparative example, wherein AGM-130 compound is intraperitoneally administered to the mouse.

FIG. 15a shows a photo and a graph indicating how the weight of tumor is changed in the A549 lung cancer xenografted model as a comparative example, wherein AGM-130 compound is intraperitoneally administered to the mouse.

As shown in FIG. 15a, the weight of tumor inoculated and grown by A549 lung cancer cells cannot be reduced significantly in a dose-dependent manner after administering AGM-130 compound.

Figure 15B:
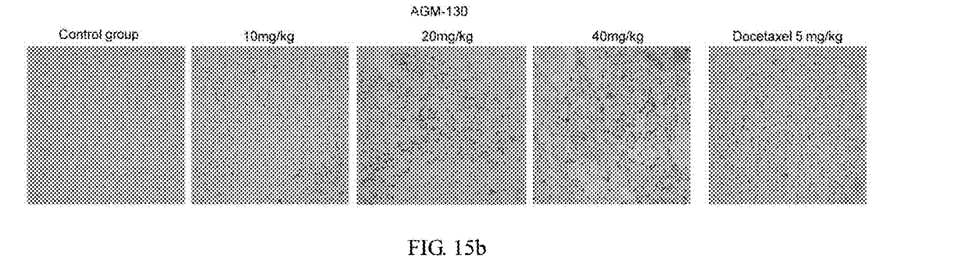
FIG. 15b shows a photo measured by TUNEL assay indicating how the shape of tumor is changed in the A549 lung cancer xenografted model as a comparative example, wherein AGM-130 compound is intraperitoneally administered to the mouse.

FIG. 15b shows a photo measured by TUNEL assay indicating how the shape of tumor is changed in the A549 lung cancer xenografted model as a comparative example, wherein AGM-130 compound is intraperitoneally administered to the mouse.

As shown in FIG. 15b, the apoptosis has been observed in the paraffin embedded tumor region. It has been shown that AGM-130 compound induces the apoptosis of A549 lung cancer cell compared to control of vehicle.

What is claimed is:

1. A method of treating breast cancer in a subject, the method comprising administering an effective amount of 5'-hydroxy-5-nitro-indirubin-3'-oxime as a cyclin-dependent kinase (CDK) inhibitor to the subject, wherein said breast cancer is a triple negative breast cancer (TNBC) and/or a tamoxifen-resistant estrogen receptor (ER) positive breast cancer.

2. The method according to claim 1, wherein said triple negative breast cancer (TNBC) is characterized in that the gene expressions of estrogen receptor (ER), progesterone receptor (PR) and Her2/neu receptor are silent.

3. The method according to claim 1, wherein said 5'-hydroxy-5-nitro-indirubin-3'-oxime inhibits the growth of cancer cells by arresting the G2/M phase in the cell cycle as well as reducing the cyclin B1 expression involved in G2/M phase in the breast cancer.

4. The method according to claim 1, wherein said 5'-hydroxy-5-nitro-indirubin-3'-oxime inhibits the growth of cancer cells by mitochondria-dependent apoptosis.

* * * * *